United States Patent [19]

Hyman et al.

[11] 4,345,079

[45] Aug. 17, 1982

[54] SCOOPABLE TRIETHYLENE DIAMINE

[75] Inventors: Floyd L. Hyman, Wilmington, Del.; Martin H. Ziv, Springfield, Pa.

[73] Assignee: Air Products and Chemicals, Inc., Allentown, Pa.

[21] Appl. No.: 142,210

[22] Filed: Apr. 21, 1980

[51] Int. Cl.$^3$ .................. C07D 487/08; C09K 3/00
[52] U.S. Cl. ..................................... 544/351; 252/382
[58] Field of Search ........................ 544/351; 252/382

[56] References Cited

U.S. PATENT DOCUMENTS

| 2,056,540 | 10/1936 | Segura | 252/382 |
| 2,937,176 | 5/1960 | Herrick | 260/268 |
| 2,977,363 | 3/1961 | Farkas et al. | 260/268 |
| 2,977,364 | 3/1961 | Mascioli | 260/268 |
| 2,985,658 | 5/1961 | Krause | 260/268 |
| 3,166,558 | 1/1965 | Mascioli | 260/268 |
| 3,646,225 | 2/1972 | Morrison | 568/702 |

FOREIGN PATENT DOCUMENTS 1429765 3/1976 United Kingdom ................ 252/382

OTHER PUBLICATIONS

Dumitrescu et al., Chem. Abs. 71, 126508f (1969).
Murata I., Chem. Abs. 86, 173457h (1977).
Blancs Mineraux de Paris, Chem. Abs. 78, 123297v (1972).
Murata II., Chem. Abs. 85, 96128b (1976).
Olevskii et al., Chem. Abs. 86, 88309s (1976).
Whitehead et al., Chem. Abs. 81, 14790s (1974).
Okamoto et al., Chem. Abs. 83, 61107a (1974).
Tsuruta et al., Chem. Abs. 74, 13578x (1970).

Primary Examiner—Mark L. Berch
Attorney, Agent, or Firm—Richard A. Dannells, Jr.; E. Eugene Innis

[57] ABSTRACT

Scoopability of triethylene diamine (TEDA) is improved by admixture therewith of a minor quantity (about 0.5 up to 2% by weight) of an additive in liquid form. The types of additives described are liquid glycol compounds selected from among polyethylene glycols, glycol esters, glycol ethers and amino alcohols. Preferred additives are: Carbowax polyethylene glycols having the general formula $$HOCH_2(CH_2OCH_2)_xCH_2OH$$

wherein x is about 3 to about 13, glycol diacetate and triethylene glycol diacetate.

11 Claims, No Drawings

SCOOPABLE TRIETHYLENE DIAMINE

BACKGROUND OF THE INVENTION

Triethylene diamine (TEDA), also known as 1,4-diazabicyclo(2.2.2) octane, is well known on the commercial market, particularly for use as a catalyst or co-catalyst in the production of polyurethane plastics, elastomers and foams. A number of methods are known to the art for preparing and isolating this compound as a product of commercially acceptable purity.

The earliest production of TEDA on a commercial scale was by the methods disclosed in U.S. Pat. No. 2,937,176, employing as starting material an alkylene polyamine. Other patented processes employ as starting material for production of TEDA, mono- or bis-hydroxyethyl piperazine (U.S. Pat. No. 3,166,558); N-aminoethyl piperazine (U.S. Pat. No. 2,985,658); or alkanolamines alone (U.S. Pat. No. 2,977,364) or in admixture with ethylene diamine (U.S. Pat. No. 2,977,363).

By any of the above methods the TEDA is isolated from the reaction mixture as a white crystalline hygroscopic product, containing a small amount of by-product amine compounds. The TEDA product is generally placed on the market for commercial users in fiber drums of about 12 gallon (about 45 liter or 25 kg.) capacity.

With improved techniques of purification of the synthesized TEDA product, by recrystallization or more precise fractionation, the product is recovered having less than about 500 ppm of accompanying by product organic amine impurities. It was found, however, that the purified commercial product of this desired low content of organic amine impurities, when stored in commercial size drum container for even short periods, particularly in a moderately warm environment, tended to form a crust or agglomerate at the top surface of the closed drum, which crust or agglomeration on further standing, penetrated further and further into the contents of the drum, rendering it difficult to scoop the product out of the drum. Without being bound to any particular explanation for the cause of this hardening of the upper layer of the TEDA in the drum, it is believed that there occurs a sublimination of the TEDA followed by its recrystallization forming a bridge between adjacent particles. This condition renders it difficult to remove product from the drum, herein referred to as poor "scoopability".

In initial attempts to avoid such hardening of the TEDA and to improve the facility of its removal ("scoopability") from the shipping containers the addition of talcs and various other additives were tried of the kinds typically employed to improve flow or prevent lumping of crystalline or powdered solid products. These substances were not found successful in improving scoopability of the TEDA product which had been exposed to temperatures above ambient. It was found, for example, that fumed or colloidal silica additives, such as Cab-O-Sil ®, when admixed and dispersed through the TEDA product at levels of 200 to 2000 ppm did obtain some improvement in the scoopability if the product remained at ambient temperature or lower. Higher levels of the Cab-O-Sil within the stated range kept the TEDA scoopable for longer time periods. At somewhat warmer temperatures, as in excess of about 35° C., the product hardened in about three days, apparently with little dependence on the level of the additive therein.

SUMMARY OF THE INVENTION

It has now been found, in accordance with the present invention, that the scoopability of triethylene diamine can be improved when there is admixed therewith a minor amount of an additive in liquid form. Generally additives having a vapor pressure approximate to that of triethylene diamine over the range of storage temperature generally encountered (i.e., 10°–50° C.) have been found most effective; however, other compounds in the desired classes with lower vapor pressures can be equally effective. The proposed additives of the invention comprise respectively polyethylene glycols, glycol ethers and esters and amino alcohols, which have a water solubility of at least 5 parts per hundred.

The preferred compounds of the invention are those which obtain good scoopability when admixed at levels of about 0.5 to 1.0% (wt/wt); also useful are compounds of the kind described which are added at somewhat higher quantity levels for desired scoopability, i.e. up to about 2.0%. With the proposed additives of the invention at the levels employed, there is not obtained the insoluble floc otherwise present when TEDA containing a silica type additive is dissolved in water or glycol.

DETAILED DESCRIPTION

The additive may be admixed with the TEDA in any manner effective to obtain good dispersion throughout the mass. The additive employed should have a viscosity higher than that of water. The preferred additives are those which do not adversely affect the appearance or performance of the TEDA or blends of TEDA; such as aqueous solutions thereof or its mixtures with dipropylene glycol or with dimethyl ethanolamine. While a certain degree of improvement in scoopability is observed when less than about 0.5% of the designated preferred additives are used; such lower additive levels have not been found to obtain the desired scoopability of the TEDA for sufficiently long storage periods.

Water solubility of the additive is important when the TEDA is employed in formulations in which it is dissolved in water, as in formulations for the production of water-blown flexible polyurethane foams. Such water-solubility is not required where the TEDA is used as catalyst in non-aqueous urethane formulations, isocyanate polymerization, or the like, provided that the additive is sufficiently soluble in the polyol or other solvent or component of the formulations with which the TEDA is to be admixed.

Among the preferred additives which in trial runs showed best results are: Carbowax-400 polyethylene glycol, glycol diacetate and triethylene glycol diacetate. Other additives that may be employed include: polyethylene glycols of lower or higher molecular weight than Carbowax 400, such as in the range of about 200 to about 600 average molecular weight, Carbitol acetate, butyl Carbitol acetate, and dimethyl ethanolamine. The useful glycol esters are those obtained by esterifying the glycol with a lower fatty acid of 1 to 3 carbon atoms; i.e. formic, acetic or propionic acid. The glycol ethers include compounds corresponding to the formula:

$$RO(C_2H_4O)_nH$$

where R is alkyl of 2 to 4 carbon atoms and n is 1 or 2. Among the useful amino alcohols are included dimethyl ethanolamine and Quadrol.

Various additives were subjected to prescreening test to determine their use for improving scoopability of plant produced TEDA having a content of co-produced amine impurities in the range of about 100 to 500 ppm. The designated additives were incorporated in the respective amounts set out in Table 1, with 3600 grams of the TEDA, and the product stored for three weeks at 120° F. (49° C.) in a quart jar.

TABLE 1

| Additive | Additive wt. grams | Storage Test Results |
|---|---|---|
| None | — | Hard |
| (1)Cab-O-Sil M-5 | 1.5 | Hard |
| (2)Quadrol | 36 | Fair Scoopability - yellow product |
| 1,4-butane diol | 36 | Fair Scoopability - turbid water solution |
| Glycol diacetate | 36 | Good scoopability - somewhat sweet odor |
| (3)Carbitol ® | 36 | Good Scoopability - Turbid water solutions |
| (4)Carbowax ® -400 | 36 | Good scoopability - clear water solution |
| (5)Butyl Cellosolve ® | 36 | Fair scoopability - turbid water solution |
| Dimethyl dodecylamine | 36 | Poor scoopability - turbid water solution |
| Dimethyl ethanolamine | 36 | Fair scoopability - yellow/tan product |

(1)Colloidal silica marketed by Cabot Corp. included herein as a control.
(2)BASF-Wyandotte tradename for N,N,N,'N'-tetrakis (2-hydroxy propyl) ethylene diamine.
(3)Union Carbide tradename for diethylene glycol monoethyl ether.
(4)Polyethylene glycols of general formula HOCH$_2$(CH$_2$OCH$_2$)$_x$CH$_2$OH, marketed by Union Carbide, wherein x ranges from about 6 to 10. The numerical designation 400 generally corresponds to the average molecular weight.
(5)"Cellosolve" is the proprietary designation of Union Carbide for glycol alkyl ethers.

Other commercial polyethylene glycol compounds available include Carbowax 200, Carbowax 300, Carbowax 600. These correspond to the general formula HOCH$_2$(CH$_2$OCH$_2$)$_x$CH$_2$OH wherein x may average from about 3 to about 13.

The turbidity of the water solutions is believed due to the limited solubility of the additive in the system. As indicated above, the formation of such water-insoluble material would be of no significance in instances where the TEDA is to be employed in non-aqueous systems. Since, in many instances, polyurethane producers may employ TEDA catalyst in aqueous as well as in non-aqueous systems, preference is had for additives obtaining clear water solutions for their admixture with TEDA. Except for possible sales resistance, the formation of yellow coloration, is not believed to have any significance as to properties of the TEDA composition containing this additive, provided such compositon has desired scoopability. As to those additives showing only fair scoopability, it is believed that scoopability could be improved by using larger proportions of the additive.

The additives which were found to perform best in the screening tests were then tried in larger scale runs. One hundred kilograms of plant-produced TEDA were added to a six cubic foot ribbon blender, which was operated for several minutes to remove lumps. At a designated time the ribbon speed was adjusted to 40 rpm and the additives listed in Table 2 were each added over a 15-30 second period. The blender was continued to run for ten minutes at 40 rpm and the mixed products discharged into 12 gallon fiber drums. These drums were stored for a week at 120° F. (49° C.) and each tested for scoopability as compared to controls (1) without additive and (2) with colloidal silica as additive.

TABLE 2

| Additive | Additive wt. gms. | Scoopability | Penetration by curved metal spatula, inches |
|---|---|---|---|
| None | — | None | 1 |
| Cab-O-Sil M-5 | 80 | None | 1 |
| Glycol diacetate | 1000 | Good | 6 |
| Carbowax -400 | 1000 | Good | 6 |

The glycol diacetate and Carbowax-400 also retained good scoopability when stored at 120° F. for several months.

A set of exploratory runs was carried out with the various additives designated in Table 3 in the amounts shown, and scoopability tested determined after storage at various temperatures for 8 weeks in half filled quart jars.

TABLE 3

| Additive | Conc. wt. % | Scoopability when stored at °F. | | |
|---|---|---|---|---|
| | | 105 | amb. | 50 |
| Quadrol | 1.2 | good (yellowish) | good | — |
| Quadrol | 0.75 | good | fair | — |
| None | — | rock-like | — | — |
| 1-butoxyethoxy-2-propanol | 1.0 | good | good | good wet appearance |
| 2-methyl-2,4-pentanediol | 1.0 | good | fair/good | good |
| Triethylene glycol diacetate | 0.5 | good | good | — |
| Triethylene glycol | 0.5 | fair | poor | — |

What is claimed is:
1. The method of improving scoopability properties of stored triethylene diamine which comprises admixing therewith a minor amount of an additive consisting essentially of a normally liquid compound selected from the group consisting of polyethylene glycols, glycol esters, glycol ethers and amino alcohols.
2. The method as defined in claim 1 wherein said triethylene diamine is admixed with 0.5% to 2% of the additive.
3. The method as defined in claim 1 or 2 wherein said additive is a polyethylene glycol of the average molecular formula

HOCH$_2$(CH$_2$OCH$_2$)$_x$CH$_2$OH wherein x is an integer of from about 3 to about 13.
4. The method as defined in claims 1 or 2 wherein said additive compound comprises glycol diacetate.
5. The method as defined in claims 1 or 2 wherein said additive comprises triethylene glycol diacetate.
6. A composition comprising triethylene diamine admixed with a minor quantity of an additive improving scoopability, said additive consisting essentially of a normally liquid compound selected from the group consisting of polyethylene glycols, glycol esters, glycol ethers and amino alcohols.
7. The composition as defined in claim 6 wherein said triethylene diamine is admixed with 0.5 to 2% of the additive.

8. The composition as defined in claim 6 wherein said triethylene diamine is admixed with up to 1% of said additive.

9. The composition as defined in claims 6, 7 or 8 wherein said additive is a polyethylene glycol of the average molecular formula $$HOCH_2(CH_2OCH_2)_xCH_2OH$$

wherein x is an integer from about 3 to about 12 or 13.

10. The composition as defined in claims 6, 7 or 8 wherein said additive comprises glycol diacetate.

11. The composition as defined in claim 7 wherein said additive comprises triethylene glycol diacetate.

* * * * *